United States Patent [19]

Warriner

[11] Patent Number: Plant 5,859

[45] Date of Patent: Jan. 20, 1987

[54] ROSE PLANT JACLOPI

[75] Inventor: William A. Warriner, Tustin, Calif.

[73] Assignee: Jackson & Perkins Company, Medford, Oreg.

[21] Appl. No.: 730,153

[22] Filed: May 3, 1985

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Manford R. Haxton

[57] ABSTRACT

A hybrid tea rose variety having rose pink buds and blooms on long, heavily prickled stems, little fragrance, long pointed leaflets.

1 Drawing Figure

This present invention relates to a new and distinct variety of rose plant of the hybrid tea class which was originated by crossing an unnamed variety with an unnamed variety.

as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

The primary objective of this breeding was to produce a new rose variety suitable for production of cut roses under greenhouse conditions with long stems, pointed buds and with a color in the pink hue. This objective was substantially achieved along with other desirable improvements as evidenced by the following unique combination of characteristics which are outstanding in the new variety and which distinguish it from its parents as well as from all other varieties of which I am aware:

1. Long stems, 18" or more, bearing pointed buds;
2. Few long prickles with many small prickles on stems;
3. Rose pink buds and blooms resembling closely the color, Red Purple 58C, of The R.H.S. Horticulture Colour Chart;
4. Very little fragrance; and
5. Relatively long, ovoid and pointed leaflets.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in February.

Blooming habit: Continuous.

Bud:

*Size.*—1½" when petals start to unfurl.

*Form.*—Pointed ovoid.

*Color.*—When sepals first divide, Near Red 55A; when half blown, upper side of petals, Near Red Purple 58C; lower side of petals, Red Purple 58C.

*Sepals.*—Color: Green 138B. Three appendaged sepals normally appendaged. Two unappendaged sepals hairy edge.

*Receptacle.*—Color: Green 138B. Shape: Funnel. Size: Large, long. Surface: Smooth.

*Peduncle.*—Length; Medium. Surface: Prickly. Color: Light green. Strength: Stiff, erect.

Open bloom:

*Size:* Large to Medium. Average open size 4½".

*Borne.*—Singly.

*Stems.*—Long, strong.

*Form.*—When first open, high center. Permanence: Flattens, outer petal edges slightly curled.

*Petalage.*—Number of petals under normal conditions: 35–40.

*Color.*—Center of flower: Upper side of petals, Near Greyed Purple 58D; reverse side of petals, Near Greyed Purple 58D. Base of petals, upper side Yellow 10B; lower side, 10D. Major color: By dictionary terms, medium pink closely equivalent to R.H.S. red Purple 58C when freshly opened, lightening to Red Purple 58D after three days.

*Variegations.*—Occasional vegetative streaks of green in outer petals.

*Fragrance.*—Very slight.

Petals:

*Texture.*—Thin.

*Shape.*—Round.

*Form.*—Edges slightly quilled.

*Arrangement.*—Imbricated

*Persistence.*—Drop off cleanly.

*Lastingness.*—On the plant, very long. As cut flower, long.

Reproductive parts:

*Anthers.*—Large, many. Color: Yellow edges with red center. Arrangement: Regular around styles.

*Filaments.*—Color: Yellow-orange.

*Pollen.*—Gold yellow.

*Styles.*—Color: Very pale green.

*Stigmas.*—Color: Red.

PLANT

Form: Bush.

Growth: Very vigorous, upright.

Foliage: Number of leaflets on normal mid-stem leaves: Usually 5.

*Size.*—Large.

*Quantity.*—Normal.

*Color.*—New Foliage: Upper side light green overlaid with Greyed Purple 184B; lower side, mostly Greyed Purple 184B. Old foliage: Near Green 137A.

Leaflets:

*Shape.*—Oval pointed.

*Texture.*—Leathery.

*Edge.*—Serrated.

*Serration.*—Single, small.

*Petiole.*—Rachis: Color: Green. Underside: With prickles.

*Stipules.*—Long, bearded.

*Disease resistance.*—Normally resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Long, hooked slightly downward.

*Color when young.*—Brown.

Small prickles:

*Quantity.*—On main stalks, many. On laterals, many.

*Color.*—Brown.

I claim:

1. A new and distinct variety of rose plant of the hybrid tea class, substantially as herein shown and described, characterized particularly as to novelty by the unique combination of its rose pink buds and blooms on long, heavily prickled stems, little fragrance, long pointed leaflets.

* * * * *

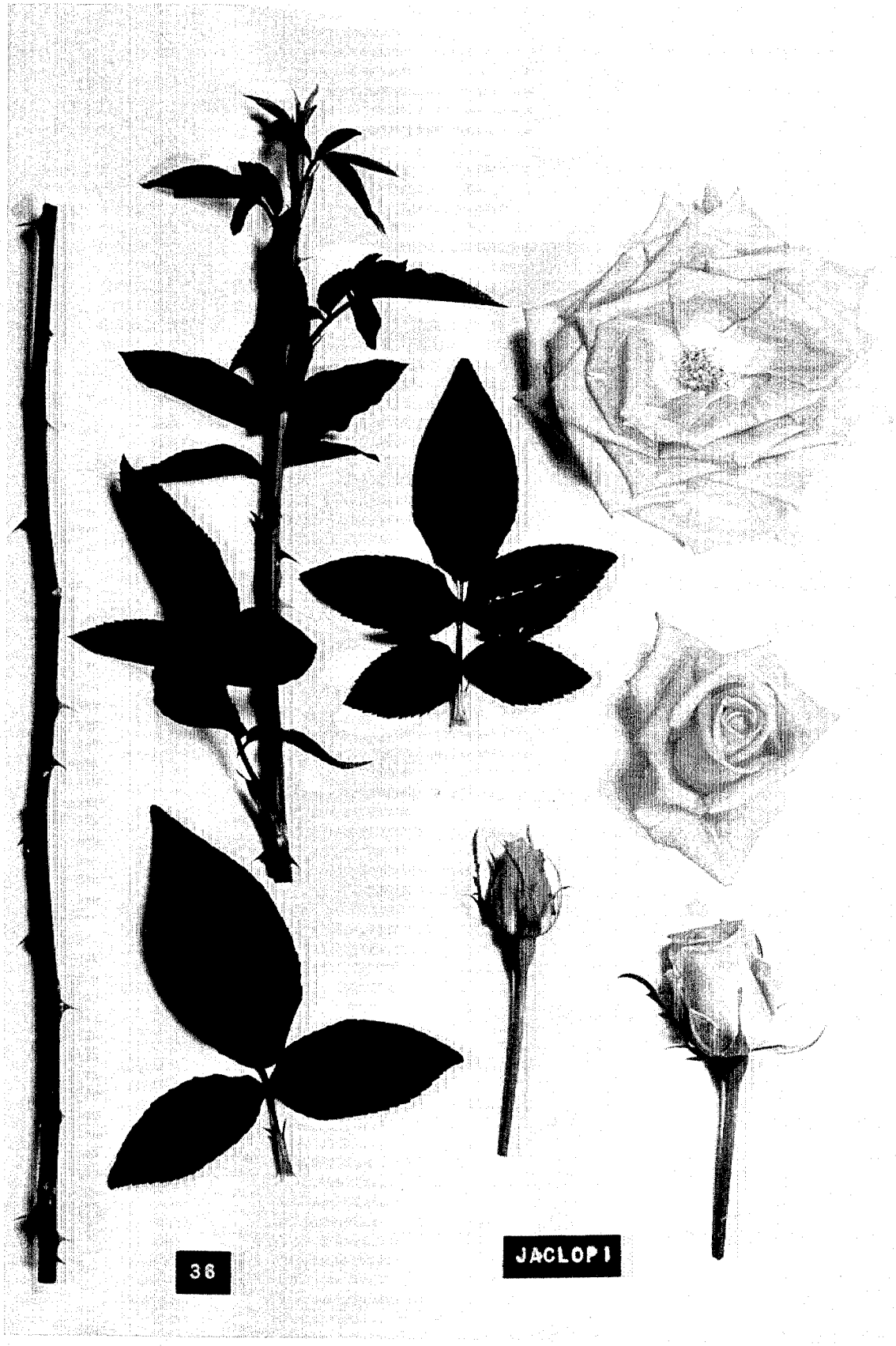
38
JACLOP1